United States Patent
Abdallah et al.

(10) Patent No.: US 10,780,139 B1
(45) Date of Patent: Sep. 22, 2020

(54) ***HYPERICUM REVOLUTUM* EXTRACT AS A VASODILATOR**

(71) Applicant: King Abdulaziz University, Jeddah (SA)

(72) Inventors: Hossam M. Abdallah, Jeddah (SA); Noha Z. Timraz, Jeddah (SA); Sabrin R. M. Ibrahim, Jeddah (SA); Ali El-Halawany, Jeddah (SA); Ibrahim A. Shehata, Jeddah (SA); Hany M. Elbassossy, Jeddah (SA)

(73) Assignee: King Abdulaziz University, Jedah (SA)

( * ) Notice: Subject to any disclaimer, the term of this patent is extended or adjusted under 35 U.S.C. 154(b) by 0 days.

(21) Appl. No.: 16/823,808

(22) Filed: Mar. 19, 2020

(51) Int. Cl.
*A61K 36/38* (2006.01)
*A61K 9/20* (2006.01)
*A61K 9/48* (2006.01)
*A61P 7/00* (2006.01)
*A61K 31/352* (2006.01)
*A61K 31/575* (2006.01)
*A61K 9/08* (2006.01)

(52) U.S. Cl.
CPC ............ *A61K 36/38* (2013.01); *A61K 9/08* (2013.01); *A61K 9/20* (2013.01); *A61K 9/4808* (2013.01); *A61K 31/352* (2013.01); *A61K 31/575* (2013.01); *A61P 7/00* (2018.01)

(58) Field of Classification Search
None
See application file for complete search history.

(56) References Cited

U.S. PATENT DOCUMENTS

| | | |
|---|---|---|
| 5,288,485 A | 2/1994 | Kikuta et al. |
| 7,195,783 B2 | 3/2007 | Shan et al. |

FOREIGN PATENT DOCUMENTS

| | | |
|---|---|---|
| GB | 1510431 | 5/1978 |

OTHER PUBLICATIONS

Câmara, et al., Phytomedicine, 17:690. (Year: 2010).*
Awad, et al., Prostaglandins, Leukotrienes and Essential Fatty Acids, 70:511. (Year: 2004).*
Capettini, et al., Planta Med., 75:145. (Year: 2009).*
Wang, et al., Phytomedicine, 16:1144. (Year: 2009).*
Ejigu, et al., Ethiop. Pharm. J., 30:21. (Year: 2014).*
Abiye et al., "Evaluation of Analgesic and Anti-Inflammatory Activities of hydro-alcoholic leaf extract of Hypericum revolutum in Mice", IJBRFA 2019; 10(03): e5071.
Luna-Vazquez et al., "Vasodilator Compounds Derived from Plants and Their Mechanisms of Action", Molecules 2013, 18, 5814-5857.
Olaiya et al., "Ameliorative effects of beta-sitosterol on some biochemical indices of hypertension in wistar albino rats", Afr J Med Med Sci. Sep. 2014; 43(Suppl 1): 157-166.

* cited by examiner

*Primary Examiner* — Michael Barker
(74) *Attorney, Agent, or Firm* — W & C IP (57) ABSTRACT

Pharmaceutical compositions comprising compounds obtainable from an extract of *Hypericum revolutum* and methods of dilating blood vessels by administering such compounds are provided.

10 Claims, 11 Drawing Sheets

HYPERICUM REVOLUTUM EXTRACT AS A VASODILATOR

FIELD OF THE INVENTION

The invention is generally related to compounds extracted from *Hypericum revolutum* and their use in methods of dilating blood vessels in subjects with hypertension (including eclampsia and preeclampsia), as well as hypertension-associated disorders (including metabolic syndrome, angina, congestive heart failure, pulmonary arterial hypertension, and erectile dysfunction).

BACKGROUND

The use of medicinal plants has formed the basis of healthcare around the globe.

Medicinal plants are becoming useful in treating different types of harmful diseases. Most developing countries, especially in Africa and Asia, have registered a significant increase in utilizing these medications. Previous reports indicated more than seventy-five percent of population treatment relies on herbal medicine (Ekor, 2014). In Saudi Arabia, the flora approximately consists of 2250 plants that are evenly distributed all over the nation (Van Slageren, 2001).

The genus *Hypericum* follows the family Clusiaceae that was previously known as Guttiferae (Xi-Wen et al., 2007). Various *Hypericum* species have exhibited antioxidant, antiviral, antibacterial, and anti-inflammatory activities (Decosterd et al., 1986; Décostered et al., 1987). The most frequently extracted compounds from this genus include chlorogenic acid, a broad range of flavonoids, naphthodianthrones, coumarins, phloroglucinols, xanthones, phenylpropanes, proanthocyanidins, benzopyrans, and benzofuran (Decosterd et al., 1986; Patocka, 2003; Shiu and Gibbons, 2009; Wang et al., 2010). *Hypericum revolutum* showed antibacterial (van Staden et al., 2017), anti-cancer (Decosterd et al., 1989), and antifungal activities (Decosterd et al., 1986).

Hypertension or the persistent increase in blood pressure is a main public health care issue in both developing and developed countries. Besides being a major health problem, it can lead to more serious and debilitating medical conditions. For example, hypertension is the leading cause of different cardiovascular diseases and has an unconstructive impact on the quality of life (M Hasan et al., 2014). Among different classes of antihypertensives, vasodilators are potent antihypertensive agents that can cause a significant reduction in blood pressure (Langford and Cox, 2007). New vasodilator compounds that can be used for the treatment of hypertension are needed.

SUMMARY

An aspect of the disclosure provides a method of dilating blood vessels in a subject in need thereof, comprising administering to the subject a therapeutically effective amount of a composition comprising i) an extract of *Hypericum revolutum* or ii) one or more compounds obtainable from an extract of *Hypericum revolutum*. In some embodiments, the subject suffers from hypertension.

In some embodiments, the composition comprises one or more of 5-dihydroxy-6-methyl-1-(3-methylbut-2-enoxy)-2-(3-methyl butyryl)-4-(2-methyl butyryl)-benzene; 3-chloro-9a-(1-hydroxy-3-methylbut-2-en-1-yl)-8-isobutyryl-2,2,7,7-tetramethyl-6-(4-methylpent-3-enoyl)hexahydro-2H-4a,8-methanocyclohepta[b]pyran-9,10(9aH)-dione; β-sitosterol; euxanthone; and 2,3,4-trimethoxy xanthone. In some embodiments, the composition is in a form selected from a tablet, capsule, or aqueous solution.

Another aspect of the disclosure provides a tablet or capsule comprising a composition comprising i) an extract of *Hypericum revolutum* or ii) one or more compounds obtainable from an extract of *Hypericum revolutum*; and a pharmaceutically acceptable carrier.

DETAILED DESCRIPTION

Figure 1:
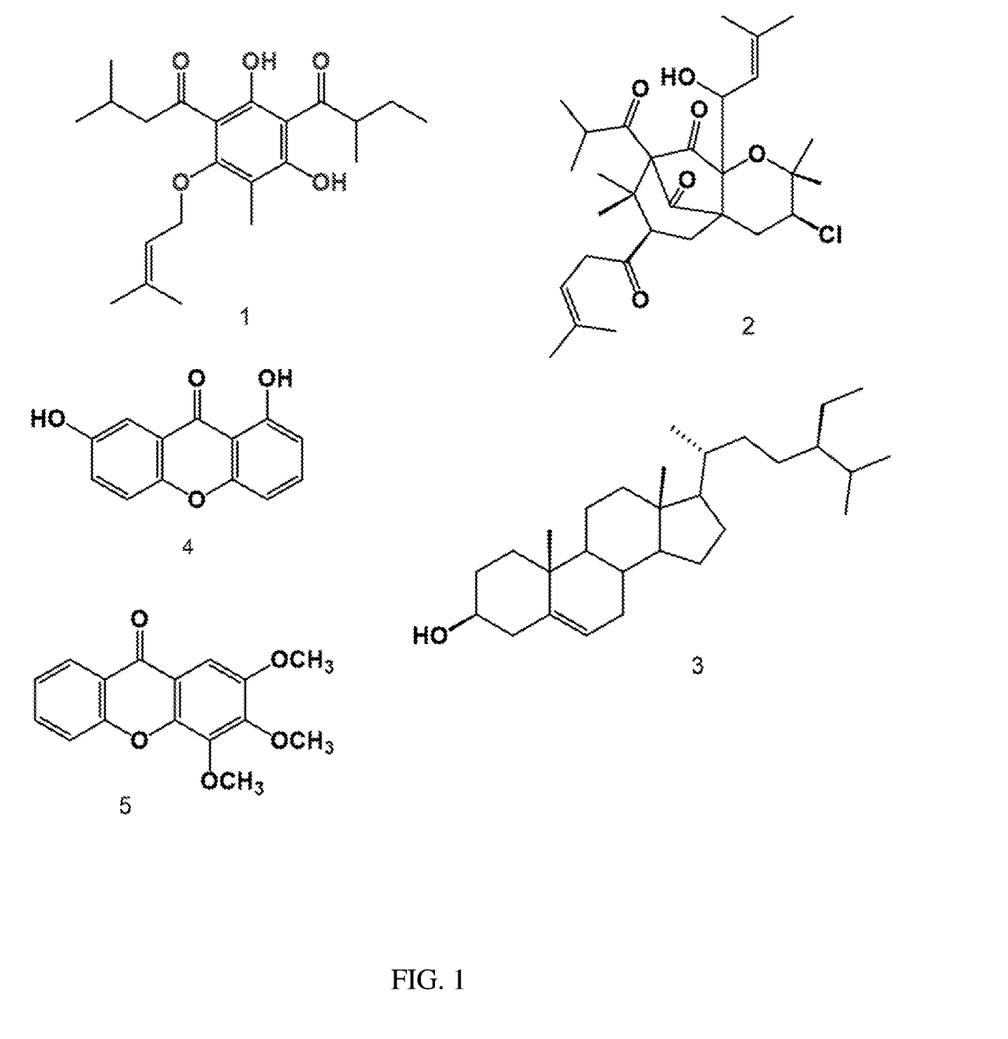
FIG. 1. Major isolated compounds from the chloroform fraction of *H. revolutum*.

Embodiments of the disclosure provide an extract of *Hypericum revolutum* or compounds obtainable (e.g. isolated or independently synthesized) from an extract of *Hypericum revolutum*. The term "synthesized" means that the compound is chemically produced (e.g. in a laboratory) as opposed to being isolated from the natural environment if it is naturally occurring. As shown in FIG. 1, compounds of the present disclosure include revolutin A (5-dihydroxy-6-methyl-1-(3-methylbut-2-enoxy)-2-(3-methyl butyryl)-4-(2-methyl butyryl)-benzene); revolutin B (3-chloro-9a-(1-hydroxy-3-methylbut-2-en-1-yl)-8-isobutyryl-2,2,7,7-tetramethyl-6-(4-methylpent-3-enoyl)hexahydro-2H-4a,8-methanocyclohepta[b]pyran-9,10(9aH)-dione); D-sitosterol; euxanthone; and 2,3,4-trimethoxy xanthone or salts or solvates thereof. The compounds described herein are effective vasodilators and may be combined with pharmaceutically acceptable adjuvants and/or carriers/excipients to prepare pharmaceutical formulations such as a tablet, capsule, or oral solution.

*Hypericum revolutum* is a shrub or small tree in the genus *Hypericum* native to Arabia and Africa. It is evergreen, with leaves opposite, closely spaced and crowded at the ends of branches, c. 20×5 mm, green to slightly glaucous, sessile, clasping at the base. An extract of this plant may be obtained by any appropriate means and in particular by extraction, preferably aqueous, alcoholic or hydro-alcoholic, by maceration, infusion, decoction, digestion, leaching or the like. An exemplary method of extraction is set forth in the Example herein.

The compositions described herein may contain one or more of the compounds as described herein. Such compositions may be prepared either as liquid solutions or suspensions, or as solid forms such as tablets, pills, granules, capsules, powders, ampoules, and the like. The liquid may be an aqueous liquid. Solid forms suitable for solution in, or suspension in, liquids prior to administration may also be prepared. The preparation may also be emulsified.

The active ingredients may be mixed with excipients which are pharmaceutically acceptable and compatible with the active ingredients. "Pharmaceutically" or "pharmaceutically acceptable" refer to molecular entities and compositions that do not produce an adverse, allergic or other untoward reaction when administered to a mammal, e.g. a human, as appropriate. A pharmaceutically acceptable carrier or excipient refers to a non-toxic solid, semi-solid or liquid filler, diluent, encapsulating material or formulation auxiliary of any type. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of the compounds in the formulations may vary. However, in general, the amount in the formulations will be from about 0.01-99%, weight/volume.

A solvate is the result of solvation which is an interaction of a solute (i.e. compound of the disclosure) with a solvent. Solvation leads to stabilization of the solute species in the solution. A solvate refers to the solvated state, whereby an ion in a solution is surrounded or complexed by solvent molecules. Exemplary solvents include, but are not limited to, propylene glycol; polypropylene glycol; polyethylene glycol (for example, polyethylene glycol 300, polyethylene glycol 400, polyethylene glycol 600, polyethylene glycol 900, polyethylene glycol 540 (all available from Union Carbide) and the like); pharmaceutically acceptable alcohols (for example, ethanol or 2-(2-ethoxyethoxy)ethanol (Transcutol®, Gattefosse, Westwood, N.J. 07675) and the like); polyoxyethylene castor oil derivatives (for example, polyoxyethyleneglycerol triricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.) and the like); fractionated coconut oil (for example, mixed triglycerides with caprylic acid and capric acid (Miglyol®812, available from Huls AG, Witten, Germany) and the like); Tween®80; isopropyl palmitate; isopropyl myristate; pharmaceutically acceptable silicon fluids; and the like.

"Salts" or "pharmaceutically acceptable salts" refers to the relatively non-toxic, inorganic and organic acid addition salts, and base addition salts, of compounds of the present disclosure. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Pharmaceutical additives can be added to increase the efficacy or potency of other ingredients in the formulation. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure also provide methods of preparing a compound or composition as described herein. The compounds described herein may be isolated or synthesized using methods known in the art.

The compounds described herein are useful as vasodilators. Thus, embodiments of the disclosure also provide methods of dilating blood vessels of a subject in need thereof by administering a compound or composition as described herein. Such methods are useful for treating subjects having conditions such as hypertension, wherein the patient has an abnormally high blood pressure (including eclampsia and preeclampsia), as well as hypertension-associated disorders (including metabolic syndrome, angina, congestive heart failure, pulmonary arterial hypertension, and erectile dysfunction). Embodiments of the disclosure include a step of identifying or diagnosing a patient in need of vasodilation, e.g. identifying a patient having hypertension as having a blood pressure above 140/90, e.g. above 180/120.

As used herein, the term "treating" includes reducing or alleviating at least one adverse effect or symptom of a disease or disorder through introducing in any way a therapeutic composition of the present disclosure into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

The compounds or compositions disclosed herein may be administered by any of the many suitable means which are well known to those of skill in the art, including but not limited to by injection, inhalation, orally, intranasally, topically, by ingestion of a food product containing the compounds, etc. In some embodiments, the mode of administration is subcutaneous or intramuscular. In addition, the compounds or compositions may be administered in conjunction with other treatment modalities such as other agents that treat hypertension, substances that boost the immune system, various chemotherapeutic agents, antibiotics, and the like.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

It should be understood that throughout the specification the term weight percent (wt %) refers to mass per unit volume, unless otherwise specified.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

Described herein are new vasodilator compounds: revolutins A (1) and B (2), in addition to β-sitosterol (3), euxanthone (4), and 2,3,4-tirmethoxy xanthone (5) extracted from *Hypericum revolutum* (Vahl). The preparation method comprises extraction of the total aerial parts of *H. revolutum* with methanol, fractionation with chloroform, then partitioning on silica gel columns using solvents with different polarities to obtain the aforementioned compounds. The compounds showed significant endothelial nitric oxide dependent vasodilation and thus are useful for treating subjects having conditions such as hypertension, (including eclampsia and preeclampsia), as well as hypertension-associated disorders (including metabolic syndrome, angina, congestive heart failure, pulmonary arterial hypertension, and erectile dysfunction).

Material and Methods
General Experimental Procedures

Shimadzu 1601 UV/VIS spectrophotometers were utilized for measuring UV spectra. Measuring the optical rotation was performed using a KRUSS polarimeter. Mass spectrometers LTQ Orbitrap and JEOL JMS-SX/SX 102A were used for low and high-resolution electrospray ionization (ESI) measurements, respectively. NMR spectra were performed on an INOVA 850 BRUKER. Chromatographic operations were done using reversed phase-18 (RP-18) and silica gel ($SiO_2$ 60) (0.04-0.063 mm). TLC plates ($SiO_2$ 60 $F_{254}$) were utilized for thin-layer chromatography (TLC).

Plant Material

The aerial parts of *Hypericum revolutum* (Vahl) were collected from Al-Baha governorate, Saudi Arabia, during April 2018. Authentication of the plant was established by Dr. Emad Al-Sharif, Associate Professor of plant ecology, Dept. of Biology, Faculty of Science & Arts, Khulais, King Abdulaziz University, Saudi Arabia. A voucher specimen (Reg. No. HR-0438) was kept at the herbarium of the Department of Natural Products and alternative medicine, Faculty of Pharmacy, King Abdulaziz University, KSA.

Extraction of Plant Material

The air-dried powdered flowering aerial parts of *H. revolutum* (1 kg) were extracted with methanol (4×5 L) at room temperature using ULTRATURRAX®, till exhaustion. Total methanol extract was evaporated under reduced pressure to give 40 g brown residue. The residue was suspended in water (200 ml) and fractionated with chloroform (4×500 ml) to give fraction I (10 g). The remaining aqueous mother liquor was evaporated (30 g), dissolved in distilled water and fractionated on polyamide column (5×110 cm, 250 g), starting with water followed by MeOH/$H_2O$ (50%) then pure MeOH, forming fractions II, III, and IV, respectively. TLC screening revealed that fraction II was free from any metabolites.

Isolation of the Major Compounds

The chloroform fraction (10 g) was chromatographed over a VLC silica gel 60 ($SiO_2$) column (10×15 cm) using n-hexane:ethyl acetate gradient elution. Fractions (100 ml, each) were collected and subjected to TLC on silica gel G plates, using solvent systems [n-hexane:EtOAc, 95:5 ($S_1$) or 90:10 ($S_2$)] and similar fractions were pooled together to give four major subfractions (A-D). Subfraction A (50 mg) (13-15, 97:3; S3) contained two major spots which gave red colour with p-anisaldehyde:$H_2SO_4$ spary reagent, which was purified on $SiO_2$ CC (2×40 cm) using $S_3$ solvent system. Similar fractions (20 ml each) were collected and subjected to TLC on silica gel G plates, using solvent system $S_1$. Fractions (5-15; 20 ml each) and fractions (20-30; 20 ml each), each contained one major spot that was further purified on RP-18 $SiO_2$ CC (1×20 cm, 3 g) using methanol:water (80:20) as a mobile phase to afford compounds 1 (colourless needles, 4 mg) and 2 (yellow amorphus solid, 20 mg). Subfraction B (100 mg) (17-20, 95:5; $S_1$) was also purified on silica gel column (2×30 cm) using n-hexane:EtOAc (95:5; $S_1$) to give two subfractions (1 and 2); each contained one blue spot as displayed on UV lamp. The solvent was evaporated under reduced pressure to yield 3 (white powder, 15 mg) and 4 (yellow needles, 12 mg). Subfraction C (100 mg) (24-26, S2 solvent system) contained one major spot as monitored by TLC. This fraction was chromatographed on $SiO_2$ CC (2×40 cm) using $S_2$ solvent system to yield compound 5 (white amorphous powder, 7 mg).

Biological Study
Drugs and Chemicals

Phenyl ephedrine (PE), acetyl choline (ACh), 2,2-diphenyl-1-picrylhydrazyl (DPPH), and dimethyl sulfoxide (DMSO) were all purchased from Sigma-Aldrich (Dorset, UK). 4-Amino-5-methylamino-2',7'-difluorofluorescein diacetate (DAF-FM) was obtained from Molecular Probes (New York, USA). Ultrapure deionized water was used as solvent except for the natural compounds and DPPH which were dissolved in DMSO in a concentration which did not exceed 0.1% in the reaction media. All other solvents and chemicals used were of analytical grade.

Experimental Animals

Male Wistar rats 6-8 weeks old (180-200 g) (King Fahd Medical Research Center, King Abdulaziz University, Jeddah, Saudi Arabia) were used in this study. Clear polypropylene cages containing 4 rats each were used to house the animals and provided access to purified water and standard rodent pellets. The animal housing conditions applied were constant involving alternating 12 hours light and dark, a temperature of 22±3° C., a relative humidity of 50-60%, and adequate ventilation. Experimental protocol was approved by the Research Ethical Committee, Faculty of Pharmacy, King Abdulaziz University, Jeddah, Saudi Arabia (approval number 126-1439) and was conducted in accordance with the Saudi Arabia Research Bioethics and Regulations.

All animals used for the purpose of this study received a standard pellet diet and drinking water. Animals were killed by decapitation with rodent guillotine and the descending thoracic aorta was carefully excised and cleaned from fat and connective tissue.

Studying the Vasodilating Activities of the Extract, Fractions, and Isolated Compounds The vasodilating activities of the methanol extract, fractions, and isolated compounds were studied using the isolated artery technique as previously described (El-Bassossy et al., 2013; El-Bassossy et al., 2016). Briefly, aorta was excised, cleaned of any fats and connective tissue, and cut into 3 mm rings. Each ring was suspended in channels filled with 25 ml of Krebs Henseleit buffer (118 mM NaCl, 4.8 mM KCl, 2.5 mM $CaCl_2$), 1.2 mM $MgSO_4$, 1.2 mM $KH_2PO_4$, 25 mM $NaHCO_3$, and 11.1 mM glucose) maintained at 37° C. and continuously aerated with gas consisting of 95% oxygen and 5% carbon dioxide. The buffer solution in the channels was changed every 30 minutes. Aortic tension was quantified by an isometric force transducer (AD Instruments, Bella Vista, Australia) and the result displayed through the PowerLab Data Interface Module connected to a PC running Chart software v8 (ADI Instruments).

The aortic rings were left to equilibrate for 20 minutes at a resting tension of 1500 mg±50. Primary contraction and relaxation of the aorta were then performed by adding PE ($10^{-5}$ M) followed by ACh ($10^{\pm 5}$ M). After the tension was returned to resting state, cumulative concentrations of the total extract, fractions (1-10 µg/ml) or the pure isolated compounds (1-10 µM) were added to the organ bath containing the isolated aortae precontracted with PE (10 µM). The decrease in tension was measured as a measure of vasodilation activities.

In another set of experiments, endothelium was mechanically denuded in order to investigate its role in the vasodilation effect.

In all experiments, similar PE-precontraction tension was achieved before testing the vasodilating responses.

Studying the Nitric Oxide Production Effect of the Extract, Bioactive Fraction, and Isolated Compounds Induction of intracellular NO production from the isolated aorta by the total extract, fraction I or the pure isolated compounds was investigated using the fluorescence probe DAF-FM as described in previous work with some modifications (Ghareib et al., 2015). Similar to previous technique, the thoracic aorta was excised, cleaned of fats, and cut into approximately 6 mm pieces. Each piece was added to a separate well in a 96-well black plate, kept in dim light, containing KHB/DAF-FM (2.5 µM) mixture (37° C.) and prepared directly before commencement of the procedure. After 3 minutes, 100 µl were carefully drawn and transferred to the adjacent column of wells after which 10 µM ACh was added to one of the aortic segments and 10 µg/ml of the total extract or fraction I or 10 µM of the pure isolated compounds was added to the other wells. Again after 3 minutes, 100 µl were drawn from the wells with the aortae and transferred to the next column of wells. For the blank, a row was kept without an aorta for each concentration of ACh was treated in the same manner. The fluorescence intensity for the withdrawn volumes (and not the column containing the aortae) was then measured at $\lambda_{ex}$=485 nm and km=515 nm with the use of Monochromator SPECTRAMAX® M3 plate reader (Molecular Devices, Sunnyvale, Calif., USA).

Studying the Antioxidant Effect of the Extract, Bioactive Fraction and Isolated Compounds The reactive oxygen species (ROS) scavenging ability of fraction I or pure isolated compounds was studied as previously reported with some modifications (Tarkhan et al., 2019). In a 96-well clear plate, the fraction I (1-10 µg/ml) or pure isolated compounds (1-10 µM) in methanol was added to DPPH solution (240 µM) in methanol/tris (1:1 v/v). For the time control (C), methanol was used instead of the fraction or compounds. DPPH was prepared immediately before addition to the plate. The absorbance was measured at 520 nm every minute for 10 minutes with the use of Monochromator SPECTRAMAX® M3 plate reader (Molecular Devices, Sunnyvale, Calif., USA).

Statistical Analysis

Experimental values were expressed as mean±SEM (standard error of the mean). For the statistical analysis, one-way or two-way analysis of variance (ANOVA) was employed as indicated in the figure legends, followed by Dunnett's post hoc test using PC running GRAPHPAD® Instat software, version 5 (GRAPHPAD® Software, Inc., La Jolla, Calif., USA). Differences were considered significant if $p<0.05$.

Results and Discussion

Chemical investigation of the $CHCl_3$ fraction of *H. revolutum* flowering aerial parts resulted in the isolation of two new metabolites (1 and 2), in addition to three known compounds (3-5) (FIG. 1). The structures of isolated compounds were identified by $^1H$ and $^{13}C$ NMR, HSQC, and HMBC, in addition to comparison with literature data. The known compounds were identified as f-sitosterol (3) (Pierre and Moses, 2015), 1,7-dihydroxyxanthone (euxanthone) (4) (Nagem and Oliveira, 1997), and 2,3,4-trimethoxy xanthone (5) (Morel et al., 2000).

Compound 1 was isolated as a yellow amorphous powder, $[\alpha]_D$+16.8 (c 0.2, MeOH). Its molecular formula was assigned to be $C_{22}H_{32}O_5$ based on the HR-ESI-MS, which displayed a pseudo-molecular peak at m/z 377.2335 $[M+H]^+$ (calcd for 377.2328, $C_{22}H_{33}O_5$).

The $^1H$ and $^{13}C$ NMR data (Table 1, FIG. 2) indicated that compound 1 was a phloroglucinol derivative (Bohlmann and Zdero, 1979; Hu et al., 2000; Rios and Delgado, 1992). The existence of a phloroglucinol skeleton was concluded from the observed three oxygen-bonded aromatic carbons at $\delta_C$ 149.9 (C-3), 162.4 (C-1), and 162.5 (C-5), and the three aromatic quaternary carbons at $\delta_C$ 104.5 (C-2), 104.3 (C-4), and 104.8 (C-6) (Rios and Delgado, 1992; Schmidt et al., 2012; Shiu et al., 2012) in the $^{13}C$ NMR spectrum. The $^{13}C$ and HSQC NMR spectra showed 22 carbon signals, consisting of seven methyls, three methylenes, three methines, and nine quaternary carbons two of them for ketone carbonyls at $\delta_C$ 205.7 (C-12) and 210.3 (C-17). Its $^1H$ and $^{13}C$ spectra revealed signals for a 3-methylbutyryl moiety at $\delta_H$ 2.94 (d, J=6.0 Hz, H-13)/$\delta_C$ 52.9 (C-13), 1.65 (m, H-14)/25.3 (C-14), 0.97 (d, J=6.8 Hz, H-15, 16)/22.8 (C-15, 16), and carbonyl at $\delta_C$ 205.7 (C-12). This was secured by the HMBC cross peak of H-13 and H-14/C-12, C-15, and C-16 and H-15 and H-16/C-13 and C-14. The HMBC (FIG. 3) showed cross peak of H-13/C-2 pointed out C-2 as an attachment position of this side chain to the phloroglucinol moiety. The observed $^1H$ signals for multiplet methine proton [$\delta_H$ 3.73 (H-18)], methylene [$\delta_H$ 1.84 and 1.41 (H-19)], primary methyl [$\delta_H$ 0.91 (t, J=6.2 Hz, H-20)], and secondary methyl [$\delta_H$ 1.16 (d, J=6.8 Hz, H-21)], correlating to the carbons at $\delta_C$ 46.0, 26.9, 12.0, and 16.7, respectively in the HSQC characterized the presence of 2-methylbutyryl moiety (Fobofou et al., 2015). The HMBC correlations of H-18/C-17, C-19, C-20, and C-21, H-19/C-17, C-18, C-20, and C-21, H-20/C-18 and C-19, and H-21/C-17, C-18, and C-19 established this assignment. The $^1$H and $^{13}$C NMR spectra exhibited signals for a tri-substituted olefinic double bond at $\delta_H$ 5.45 (H-8)/$\delta_C$ 119.2 (C-8), an oxymethylene at $\delta_H$ 4.52 (H-7)/$\delta_C$ 65.3 (C-7), and two methyls at $\delta_H$ 1.79 (H-10)/25.8 (C-10) and 1.73 (H-11)/18.3 (C-11), indicating the existence of 3-methylbut-2-enoxy moiety in compound 1. This was assured by the observed HMBC cross peaks (Bohlmann and Suwita, 1978, 1979). Its attachment to C-1 was confirmed based on the HMBC cross peak of H-7 to C-1. Moreover, a methyl signal at $\delta_H$ 2.02 (H-22), correlating to the carbon $\delta_C$ 7.3 (C-22) in the HSQC and showing HMBC cross peaks to C-1, C-5, and C-6 established the existence of an aromatic methyl at C-6. Finally, compound 1 was identified as 3,5-dihydroxy-6-methyl-1-[(3-methylbut-2-en-1-yl)oxy]-2-(3-methyl butyryl)-4-(2-methyl butyryl)-benzene and given the name revolutin A based on comparing its data to the literature (Bohlmann and Suwita, 1978, 1979).

TABLE 1

NMR spectral data of compound 1 (CDCl$_3$, 850 and 214 Hz)

| No. | $\delta_H$ (mult., J (Hz)) | $\delta_C$ (mult.) | HMBC |
|---|---|---|---|
| 1 | — | 162.4 C | |
| 2 | — | 104.5 C | |
| 3 | — | 149.9 C | |
| 4 | — | 104.3 C | |
| 5 | — | 162.5 C | |
| 6 | — | 104.8 C | |
| 7 | 4.52 d (6.0) | 65.3 CH$_2$ | 1, 8,9, 10, |
| 8 | 5.45 m | 119.2 CH | 7, 14, 15 |
| 9 | — | 138.3 C | — |
| 10 | 1.79 s | 25.8 CH$_3$ | 8, 9, 11 |
| 11 | 1.73 s | 18.3 CH$_3$ | 8, 9, 10 |
| 12 | — | 205.7 C | — |
| 13 | 2.94 d (6.0) | 52.9 CH$_2$ | 12, 14, 20, 21 |
| 14 | 1.65 m | 25.3 CH | 12, 15, 16 |
| 15 | 0.97 d (6.8) | 22.8 CH$_3$ | 13, 14 |
| 16 | 0.97 d (6.8) | 22.8 CH$_3$ | 13, 14 |
| 17 | — | 210.3 C | — |
| 18 | 3.73 m | 46.0 CH | 4, 17, 19, 20, 21 |
| 19 | 1.84 m<br>1.41 m | 26.9 CH$_2$ | 18, 19, 20, 21 |
| 20 | 0.91 t (6.2) | 12.0 CH$_3$ | 18, 19 |
| 21 | 1.16 d (6.8) | 16.7 CH$_3$ | 17, 18, 19 |
| 22 | 2.02 s | 7.3 CH$_3$ | 1, 5, 6 |

Compound 2 was isolated as a yellow amorphous solid. Its HR-ESI-MS displayed two pseudo-molecular ion peaks at m/z 535.2816 (C$_{30}$H$_{45}$$^{35}$ClO$_6$, [M+H]$^+$) and 537.2821 (C$_{30}$H$_{45}$$^{37}$ClO$_6$, [M+H]$^+$) in a ratio of 3:1, indicating the presence of a chlorine atom in 2 (Ibrahim et al., 2015). The molecular formula C$_{30}$H$_{44}$ClO$_6$ suggested nine degrees of unsaturation.

$^1$H NMR spectra (Table 2) showed signals for four quaternary methyls at $\delta_H$ 1.24 (H-14), 1.26 (H-12), 1.28 (H-13), and 1.38 (H$_3$-11), two γ,γ-dimethyl allyl, two secondary methyls at $\delta_H$ 1.09 (d, J=6.8 Hz, H-18) and 1.10 (d, J=7.0 Hz, H-17) in addition to an oxymethine (H-19), a methine (H-3), and three methylenes (H-4, H-5, and H-25).

Figure 2:
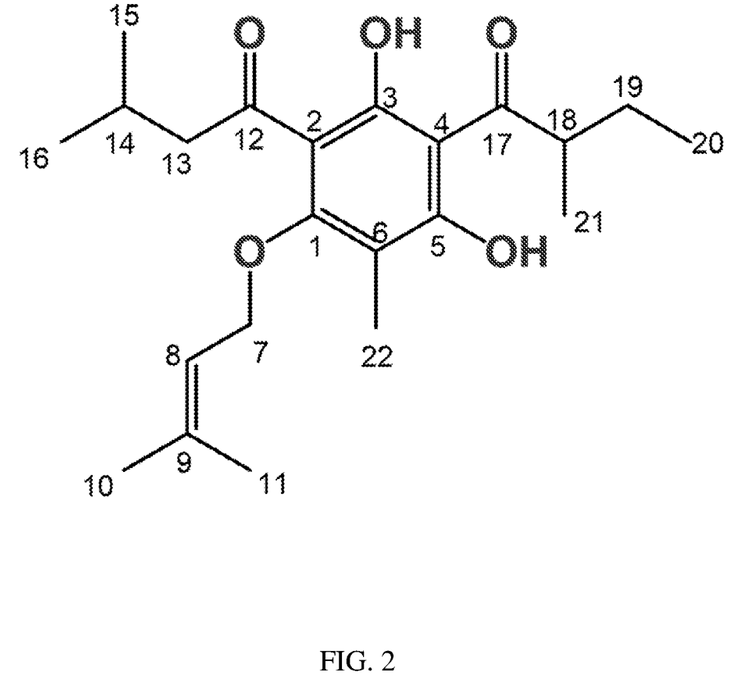
FIG. 2. Chemical structure of compound 1.
Figure 3:
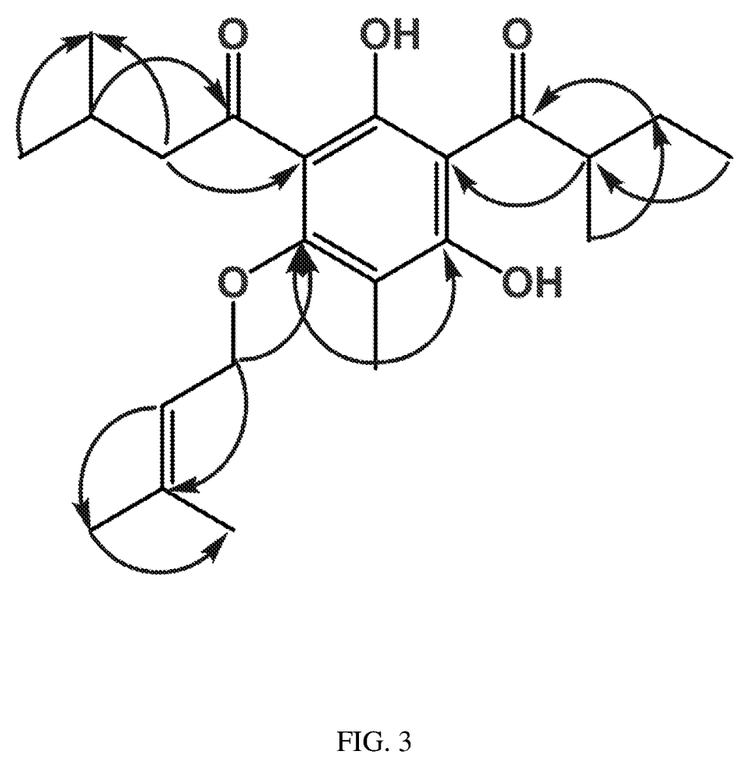
FIG. 3. HMBC correlations of compound 1.

Its $^{13}$CNMR and HSQC spectra showed the presence of ten methyls, three methylenes, six methines (from which two olefinics and one oxymethine), and eleven quaternary carbons including four carbonyls. $^1$H-$^1$H COSY of showed correlations between H-20/H19, H-4/H-3, H-25/H-26, and H-16/H-17 and H-18 that established the partial moieties represented in bold lines (FIG. 2). HMBC correlations between H-25/C-6, C-24, and C-27 established connectivity between C-6 and C-24, C-26 and C-25 and confirmed the attachment of the 1-oxo-4-methyl-pent-3-eneyl moiety to C-6. In addition, correlations between H-26/H-28 and H-29 confirmed the connection of γ,γ-dimethyl allyl to C-25. Moreover, the correlations between H-5/C-24 and C-7 confirmed the connectivity between carbons 5, 6, and 7. The HMBC correlations of H-16-15/C-17 and C-18 and H-13 and H-14/C-6 and C-8, H-16/C-8, in addition to the correlation between H-6 and C-8 established the connectivity between C-7/C-8, and C-6/C-7 and confirmed the attachment of the 1-oxo-2-methyl propyl group to C-8. Moreover, the observed HMBC correlations between H-4/C-9a, C-4a, C-10, C-2, and C-5 and H-11 and H-12/C-2 established the 3,4-dihydropyran moiety and connectivity between C-4a and C-10. These findings revealed that the pyran ring should be fused between C-9a and C-4a. The HMBC correlations of H-20/C-22 and C-23, H-22, H-23 and H-19/C-21, and H-19/C-9 and C-4a confirmed that the second γ,γ-dimethyl ally group was linked to C-9a through an oxymethine (C-19). The attachment of chloride to C-3 was confirmed by the downfield shift of H-3/C-3.

Figure 4A:
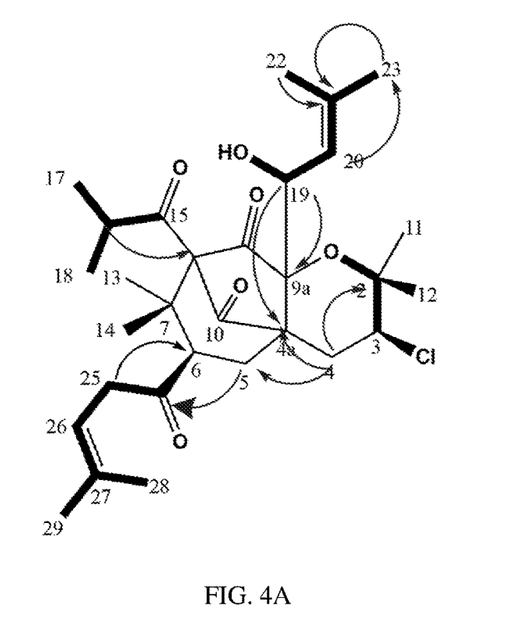
FIG. 4A-B. HMBC (A) and NOESY (B) correlations of compound 2.
Figure 4B:
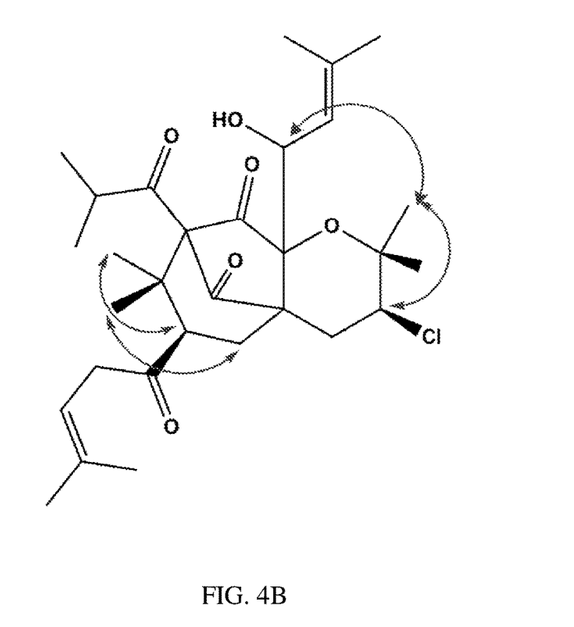

Moreover, the NOESY experiment of (FIG. 4) showed significant cross peaks between HP-4/H-12, H-11/H-3, H-11/H-19, Hβ-5/H-14, and H-6/H-13 suggested the placement of H-11, H-3, H-6, H-13, H-19, and H-16 in the same side of the molecule. On the basis of the previously mentioned data, the structure of 2 was assigned as 3-chloro-9a-(1-hydroxy-3-methylbut-2-en-1-yl)-8-isobutyryl-2,2,7,7-tetramethyl-6-(4-methylpent-3-enoyl)hexahydro-2H-4a,8-methanocyclohepta[b]pyran-9,10(9aH)-dione and the name revolutin B was given to it.

TABLE 2

NMR spectral data of compound 2 (CDCl$_3$, 850 and 214 Hz)

| No. | $\delta_H$ (mutt., J (Hz)) | $\delta_C$ (mult.) |
|---|---|---|
| 2 | — | 83.0 C |
| 3 | 2.40 dd (11.6, 8.3) | 54.8 CH |
| 4 | 2.12 dd (15.2, 11.6)<br>1.77 dd (15.2, 8.3) | 25.6 CH$_2$ |
| 4a | — | 67.9 C |
| 5 | 2.44 dd (15.1, 7.0)<br>1.92 d (15.0) | 34.9 CH$_2$ |
| 6 | 1.96 t (7.0) | 42.4 CH |
| 7 | — | 46.7 C |
| 8 | — | 86.5 C |
| 9 | — | 199.6 C |
| 9a | — | 76.9 C |
| 10 | — | 202.4 C |
| 11 | 1.38 s | 31.1 CH$_3$ |
| 12 | 1.26 s | 25.3 CH$_3$ |
| 13 | 1.28 s | 22.2 CH$_3$ |
| 14 | 1.24 s | 24.6 CH$_3$ |
| 15 | — | 207.0 C |
| 16 | 1.78 m | 44.3 CH |
| 17 | 1.10 d (6.8) | 21.1 CH$_3$ |
| 18 | 1.09 d (6.8) | 20.7 CH$_3$ |
| 19 | 5.57 d (9.0) | 74.7 CH |
| 20 | 5.36 dt (9.0, 1.5) | 119.8 CH |
| 21 | — | 140.0 C |
| 22 | 1.63 s | 26.3 CH$_3$ |
| 23 | 1.75 s | 18.8 CH$_3$ |
| 24 | — | 204.1 C |
| 25 | 2.51 d (7.5) | 28.7 CH$_2$ |
| 26 | 5.22 brt (7.5) | 118.7 CH |
| 27 | — | 135.5 C |
| 28 | 1.73 s | 18.2 CH$_3$ |
| 29 | 1.73 s | 26.2 CH$_3$ |

Vasodilating Activity of the Total Extract and Chloroform Fraction (I)

Figure 5:
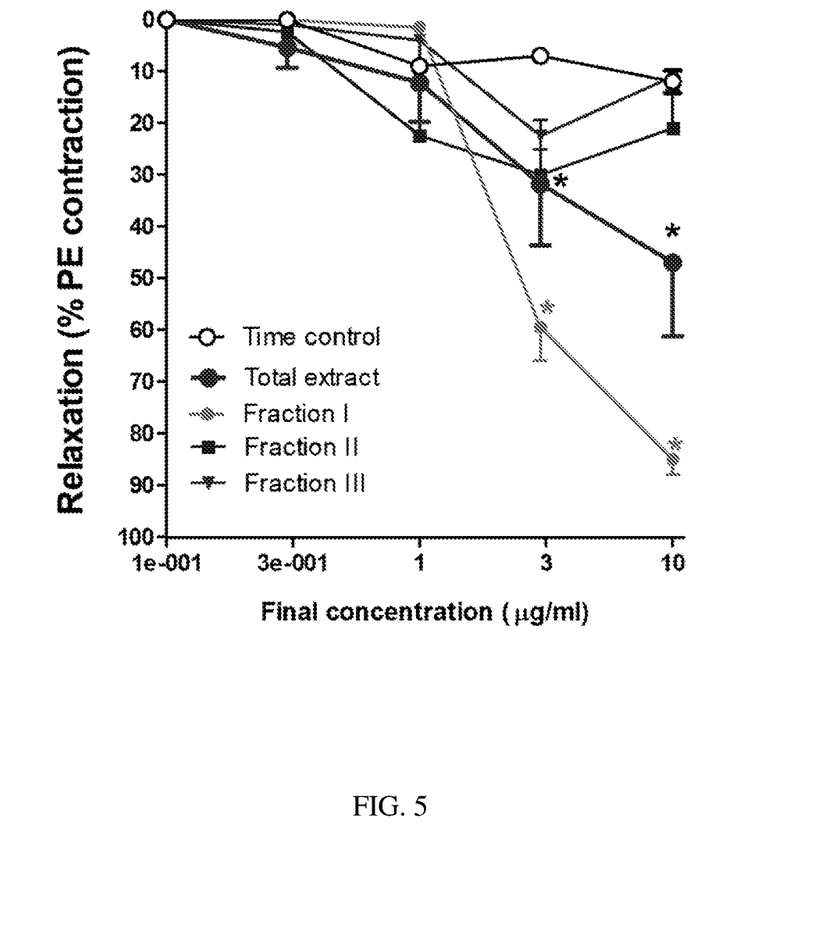
FIG. 5. Effect of *H. revolutum* total extract and fractions on PE pre-contracted isolated aorta. Results are expressed as mean±SEM (n=8). * Significantly different from the corresponding time control values at $p<0.05$; by two-way repeated measures ANOVA and Newmans Keuls post hoc test.

Total methanol extract of *H. revolutum* brought about a decrease in tension and hence concentration dependent vasodilation of phenylephrine (PE, $10^{-6.5}$ M) precontracted isolated aorta that reached statistical significance (p<0.05) at concentrations of 3 and 10 µg/ml (FIG. 5). The bio-guided fractions revealed that fraction I (chloroform fraction) is responsible for the observed vasodilation activity of the total extract as the addition of fraction I led to similar vasodilation that reached statistical significance (p<0.05) at concentrations of 3 and 10 µg/ml (FIG. 5).

Figure 6A:
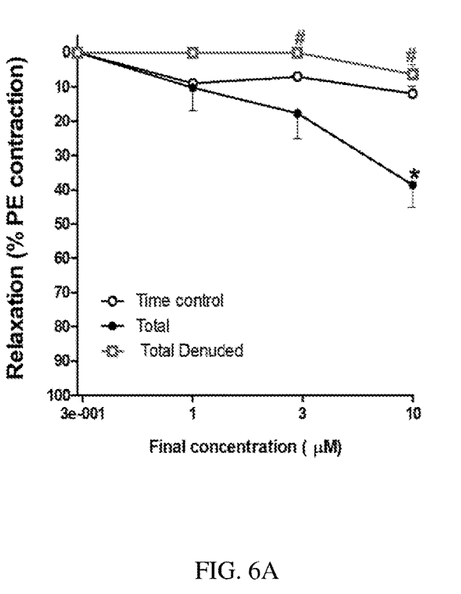
FIG. 6A-B. Effect of *H. revolutum* total extract (A) and fraction I (B) on PE pre-contracted isolated normal and endothelium-denuded aorta. Results are expressed as mean±SEM (n=8). * significantly different from the corresponding time control values at $p<0.05$; # significantly different from the corresponding total extract or fraction I values at $p<0.05$; by two-way repeated measures ANOVA and Newmans Keuls post hoc test.
Figure 6B:
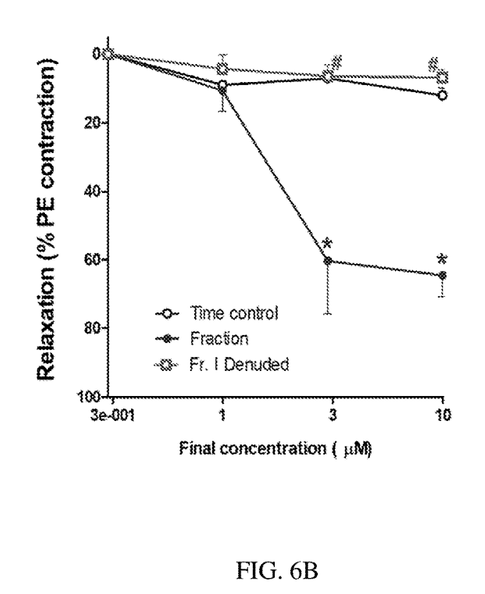

Aorta denudation (endothelial layer removal) blocked the vasodilating activity of the total extract of *H. revolutum* as observed from the significant inhibition at concentrations of 3 and 10 µg/ml (both at p<0.05, FIG. 6A). Similarly, endothelial denudation blocked the vasodilation activity of fraction I as observed from the significant inhibition at concentrations of 3 and 10 µg/ml (both at p<0.05, FIG. 6B).

Vasodilating Activity of the Isolated Compounds

Figure 7A:
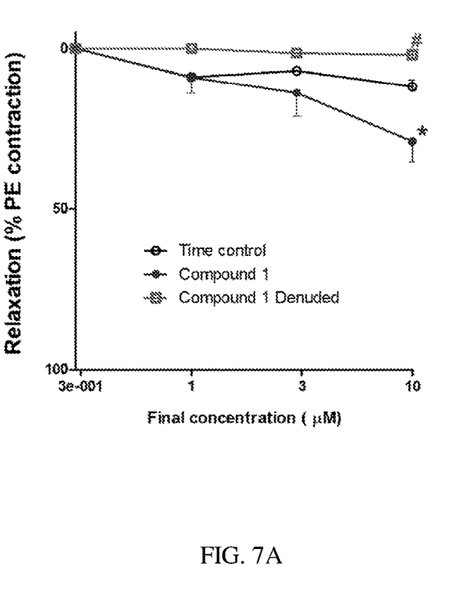
FIG. 7A-B. Effect of compounds 1 (A) and 2 (B) in the absence or presence of the nitric oxide synthase inhibitor (L-NAME, 1 mM) and endothelial denudation on PE pre-contracted isolated aorta. Results are expressed as mean±SEM (n=8). * Significantly different from the corresponding time control values at $p<0.05$; # significantly different from the corresponding compound 1 or 2 values at $p<0.05$; by two-way repeated measures ANOVA and Newmans Keuls post hoc test.

FIG. 7A showed that compound 1 led to a concentration dependent vasodilation of phenylephrine (PE, $10^{-6.5}$ M) precontracted isolated aortae that reached statistical significance at a concentration of 10 µM (p<0.05). Endothelial denudation completely blocked the vasodilation activity of compound 2 as made apparent by the significant inhibition at a concentration of 10 µM (p<0.05, FIG. 7A).

Figure 7B:
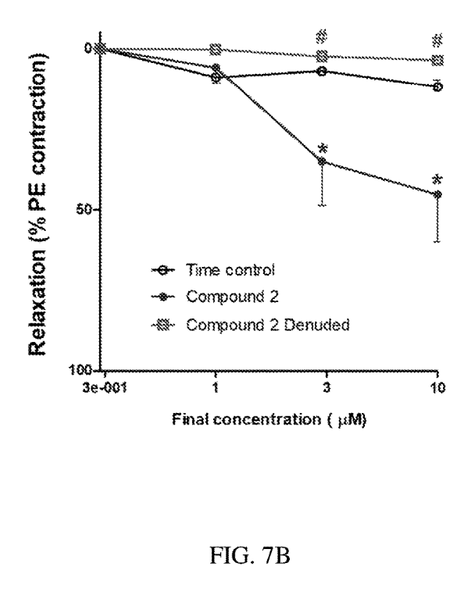

Compound 2 produced a greater vasodilation (reaching 50%) of PE-precontracted isolated aortae that reached statistical significance at concentrations of 3 and 10 µM (both at p<0.05, FIG. 7B).

Figure 8A:
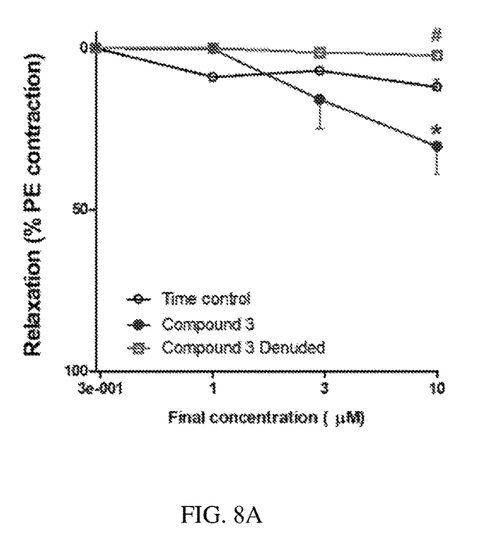
FIG. 8A-C. Effect of compounds 3 (A), 4 (B), and 5 (C) in the absence or presence of the nitric oxide synthase inhibitor (L-NAME, 1 mM) and endothelial denudation on PE pre-contracted isolated aorta. Results are expressed as mean±SEM (n=8). * Significantly different from the corresponding time control values at $p<0.05$; # significantly different from the corresponding compound 3, 4 or 5 values at $p<0.05$; by two-way repeated measures ANOVA and Newmans Keuls post hoc test.

Addition of the compound (3) led to a concentration dependent vasodilation of phenylephrine (PE, $10^{-6.5}$ M) precontracted isolated aortae. The vasodilation effect of the compound 3 reached statistical significance (p<0.05) at a concentration of 10 µM. Endothelial denudation completely blocked the vasodilation activity of compound 3 as observed from the significant inhibition at a concentration of 10 µM (p<0.05, FIG. 8A).

Figure 8B:
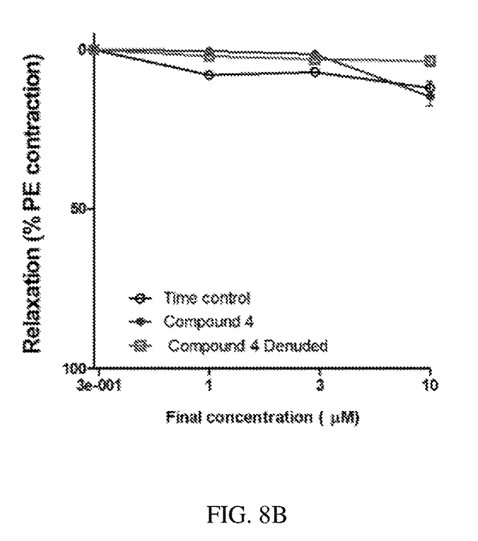

However, compound 4 did not show any significant vasodilation of PE ($10^{-5}$ M) precontracted isolated aortae and endothelial denudation did not have any significant effect (FIG. 8B).

Figure 8C:
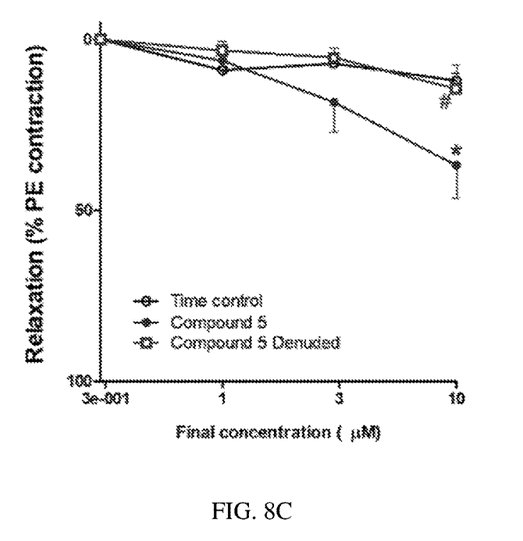

FIG. 8C showed that the addition of the compound 5 brought about a decrease in tension and hence concentration dependent vasodilation of PE ($10^{-6.5}$ M) precontracted isolated aortae. The vasodilation effect of 5 reached statistical significance (p<0.05) at a concentration of 10 µM. Similarly, endothelial denudation blocked the vasodilation activity of compound 5 as observed from the significant inhibition at a concentration of 10 µM (p<0.05).

The Effect on Vascular NO Production

Figure 9:
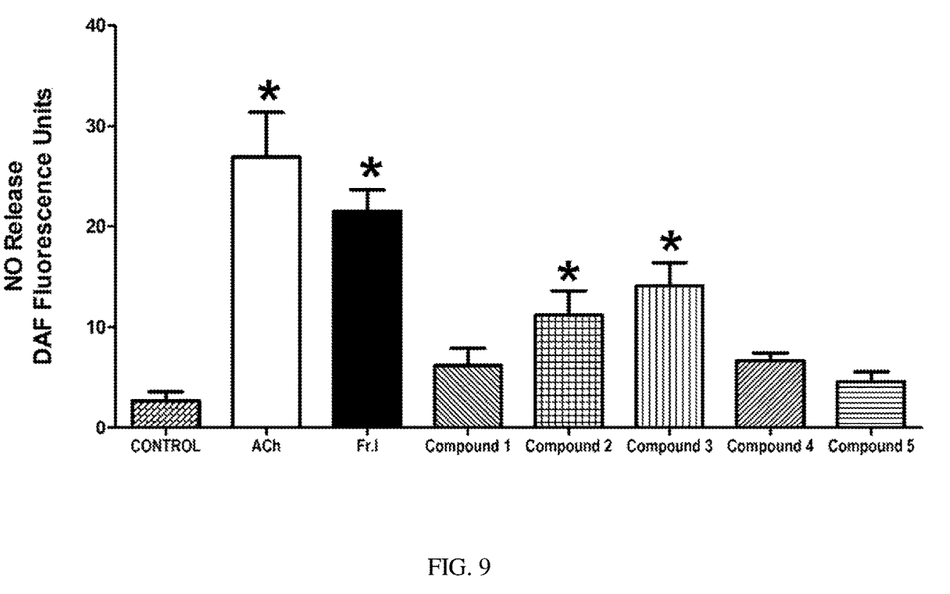
FIG. 9. Effect of *H. revolutum*, fraction I (10 μg/ml) and compounds 1-5 all at a concentration of 10 μM on vascular NO production in comparison to Ach (10 μM). * significantly different from the control value at $P<0.05$; by one way ANOVA and Newmans Keuls post hoc test.
Figure 10A:
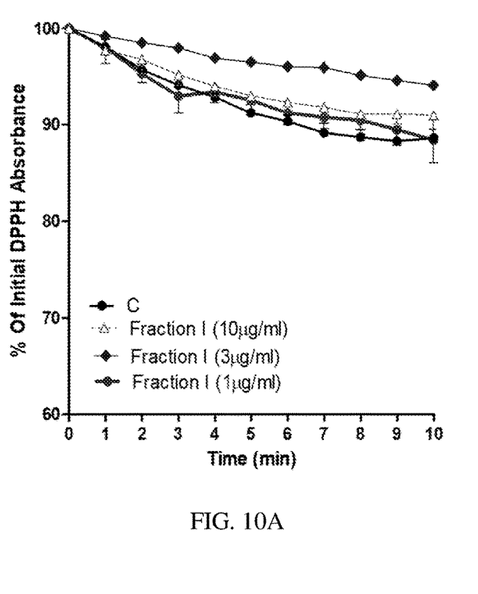
FIG. 10A-F. Effect of Fraction I (A) and isolated compounds 1 (B), 2 (C), 3 (D), 4 (E), and 5 (F) on ROS production as initiated by DPPH (240 μM). Control (C) is a reaction mixture including only DPPH. Results are expressed as mean±SEM (n=3). * $P<0.05$ when compared to each corresponding control; by two-way repeated measures ANOVA and Newmans Keuls post hoc test.
Figure 10B:
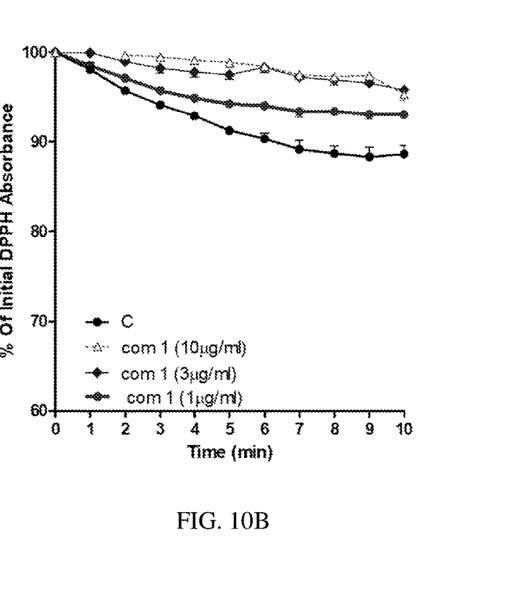
Figure 10C:
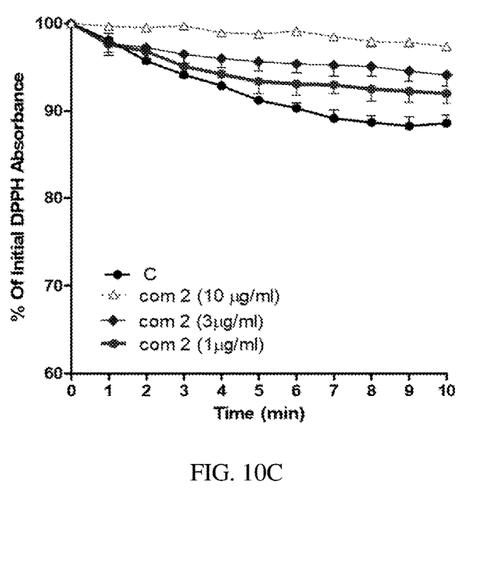
Figure 10D:
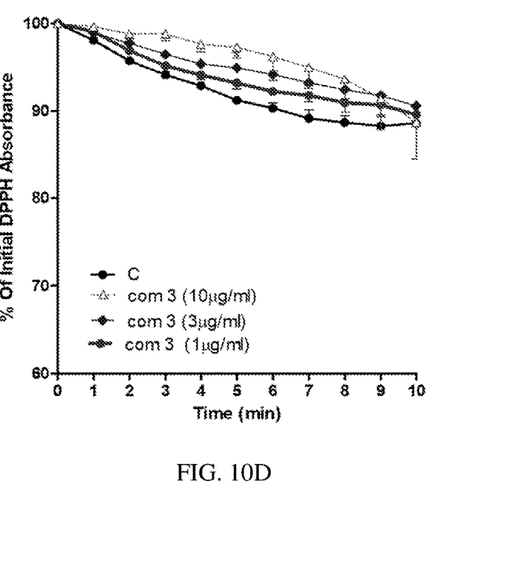
Figure 10E:
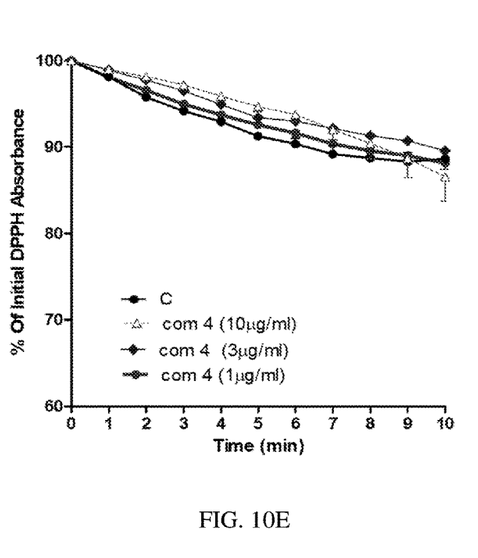
Figure 10F:
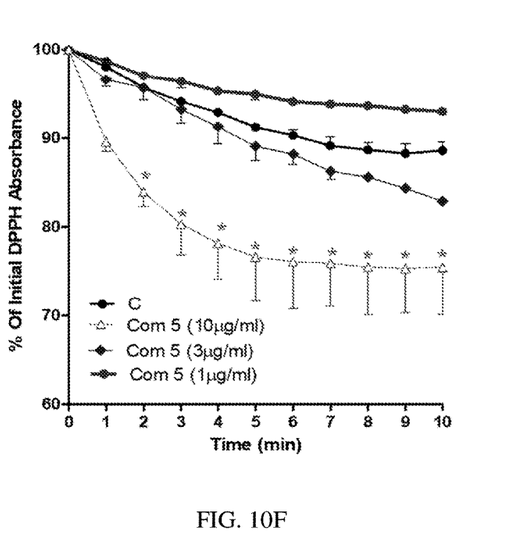

As observed from the graph (FIG. 9), the addition 10 µM of Ach to the aortic rings at 37° C. resulted in a significant (p<0.05) NO production compared with control, detected and quantified by DAF-FM reagent (2.5 µM). Addition of the fraction I at a concentration of 10 µg/ml led to a similar increase in NO production as observed from the significant increase in DAF-FM fluorescence compared with control values (p<0.05). The isolated compounds induced NO production that reached statistical significance (all at p<0.05) with compounds 2 and 3 at a concentration of 10 µM (FIG. 9).

The Free Radical Scavenging Activity

FIG. 10 displayed the results of a 10-minute reaction between DPPH (240 µM), fraction I, and compounds 1-5 at three different concentrations (1, 3, and 10 µM). Among the tested compounds, only compound 5 showed a significant free radical scavenging activity. FIG. 10 showed that at a concentration of 10 µM, compound 5 possessed DPPH free radical scavenging activity which is translated into an antioxidant effect as observed from the significant differences from control starting from the second minute until minute 10 (p<0.05).

ACKNOWLEDGEMENT

This project was funded by Science and Technology Unit—King Abdulaziz University—Kingdom of Saudi Arabia—award number (UE-41-115).

REFERENCES

Bohlmann, F., Suwita, A., 1978. Neue phloroglucin-derivate aus Leontonyx-arten sowie weitere verbindungen aus vertretern der tribus inuleae. Phytochemistry 17, 1929-1934.

Bohlmann, F., Suwita, A., 1979. Weitere phloroglucin-derivate aus *Helichrysum*-arten. Phytochemistry 18, 2046-2049.

Bohlmann, F., Zdero, C., 1979. Neue phloroglucin-derivate aus *Helichrysum natalitium* und *Helichrysum bellum*. Phytochemistry 18, 641-644.

Decosterd, L. A., Stoeckli-Evans, H., Msonthi, J. D., Hostettmann, K., 1986. A New Antifungal Chromene and a Related Di-chromene from *Hypericum revolutum*. Planta Med., 429.

Decosterd, L. A., Stoeckli-Evans, H., Chapuis, J. C., Msonthi, J. D., Sordat, B., Hostettmann, K., 1989. New Hyperforin Derivatives from *Hypericum revolutum* Vahl with Growth-Inhibitory Activity Against a Human Colon Carcinoma Cell Line. Helv. Chim. Acta 72, 464-471.

Décostered, L. A., Hostettmann, K., Stoeckli-Evans, H., Msonthi, J. D., 1987. New antifungal chromenyl ketones and their pentacyclic dimers from *Hypericum revolutum* Vahl. Helv. Chim. Acta 70, 1694-1702.

Ekor, M., 2014. The growing use of herbal medicines: issues relating to adverse reactions and challenges in monitoring safety. Front. Pharmacol. 4, 177.

El-Bassossy, H. M., El-Fawal, R., Fahmy, A., Watson, M. L., 2013. Arginase inhibition alleviates hypertension in the metabolic syndrome. British Journal of Pharmacology 169, 693-703.

El-Bassossy, H. M., Elberry, A. A., Ghareib, S. A., 2016. Geraniol improves the impaired vascular reactivity in diabetes and metabolic syndrome through calcium channel blocking effect. J. Diabetes Complications 30, 1008-1016.

Fobofou, S. A., Franke, K., Sanna, G., Porzel, A., Bullita, E., La Colla, P., Wessjohann, L. A., 2015. Isolation and anticancer, anthelminthic, and antiviral (HIV) activity of acylphloroglucinols, and regioselective synthesis of empetrifranzinans from *Hypericum roeperianum*. Bioorganic Medicinal Chemistry 23, 6327-6334.

Ghareib, S. A., El-Bassossy, H. M., Elberry, A. A., Azhar, A., Watson, M. L., Banjar, Z. M., 2015. 6-Gingerol alleviates exaggerated vasoconstriction in diabetic rat aorta through direct vasodilation and nitric oxide generation. Drug design, development and therapy 9, 6019.

Hu, L. H., Khoo, C. W., Vittal, J. J., Sim, K. Y., 2000. Phloroglucinol derivatives from *Hypericum japonicum*. Phytochemistry 53, 705-709.

Ibrahim, S. R., Mohamed, G. A., Moharram, A. M., Youssef, D. T., 2015. Aegyptolidines A and B: New pyrrolidine alkaloids from the fungus *Aspergillus aegyptiacus*. Phytochem. Lett. 12, 90-93.

Langford, N.J., Cox, A., 2007. Chapter 87—Interactions Between Antihypertensive Drugs and Other Medications, in: Lip, G. Y. H., Hall, J. E. (Eds.), Comprehensive Hypertension. Mosby, Philadelphia, pp. 1075-1086.

M Hasan, D., H Emeash, A., B Mustafa, S., Abdelazim, E. A., Alaa El-din, A., 2014. Hypertension in Egypt: a systematic review. Current hypertension reviews 10, 134-141.

Morel, C., Séraphin, D., Oger, J.-M., Litaudon, M., Sévenet, T., Richomme, P., Bruneton, J., 2000. New xanthones from *Calophyllum caledonicum*. J. Nat. Prod. 63, 1471-1474.

Nagem, T. J., Oliveira, F. F. d., 1997. Xanthones and other constituents of *Vismia parviflora*. J. Braz. Chem. Soc. 8, 505-508.

Neamsuvan, O., Komonhiran, P., Boonming, K., 2018. Medicinal plants used for hypertension treatment by folk healers in Songkhla province, Thailand. Journal of Ethnopharmacol 214, 58-70.

Patocka, J., 2003. The chemistry, pharmacology, and toxicology of the biologically active constituents of the herb *Hypericum perforatum* L. Journal of Applied Biomedicine 1, 61-70.

Pierre, L. L., Moses, M. N., 2015. Isolation and characterisation of stigmasterol and β-sitosterol from *Odontonema strictum* (Acanthaceae). Journal of Innovations in Pharmaceuticals and Biological Sciences 2, 88-96.

Rios, M. Y., Delgado, G., 1992. Polyprenols and acylphloroglucinols from *Esenbeckia nesiotica*. Phytochemistry 31, 3491-3494.

Schmidt, S., Jiirgenliemk, G., Schmidt, T. J., Skaltsa, H., Heilmann, J., 2012. Bi-, Tri-, and Polycyclic Acylphloroglucinols from *Hypericum empetrifolium*. J. Nat. Prod. 75, 1697-1705.

Shiu, W. K., Rahman, M. M., Curry, J., Stapleton, P., Zloh, M., Malkinson, J. P., Gibbons, S., 2012. Antibacterial acylphloroglucinols from *Hypericum olympicum*. J. Nat. Prod. 75, 336-343.

Shiu, W. K. P., Gibbons, S., 2009. Dibenzofuran and pyranone metabolites from *Hypericum revolutum* ssp. *revolutum* and *Hypericum choisianum*. Phytochemistry 70, 403-406.

Tarkhan, M. M., Balamsh, K. S., El-Bassossy, H. M., 2019. Cinnamaldehyde protects from methylglyoxal-induced vascular damage: Effect on nitric oxide and advanced glycation end products. J. Food Biochem., e12907.

Van Slageren, M., 2001. Wildflowers of Saudi Arabia. Kew Bulletin 56, 1021.

van Staden, A. B., De Canha, M., Nqephe, M., Rademan, S., Kumar, V., Lall, N., 2017. Potential medicinal plants for progressive macular hypomelanosis. S. Afr. J. Bot. 111, 346-357.

Wang, D., Bai, J., Sun, F., Yang, D., 2010. Chemical constituents and antidepressant activity of the new species *Hypericum enshiense* occurring in China. Phytomedicine 17, 410-413.

Xi-Wen, L., Jie, L., Robson, N. K., Stevens, P. F., 2007. Clusiaceae (guttiferae). Flora of China 13, 1-47.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of dilating blood vessels in a subject in need thereof, comprising administering to the subject a therapeutically effective amount of a composition comprising i) an extract of *Hypericum revolutum* or ii) one or more compounds obtainable from an extract of *Hypericum revolutum* or salts or solvates thereof, wherein the composition comprises 2,3,4-trimethoxy xanthone.

2. The method of claim 1, wherein the subject suffers from one or more of hypertension, eclampsia, preeclampsia, metabolic syndrome, angina, congestive heart failure, pulmonary arterial hypertension, and erectile dysfunction.

3. A method of dilating blood vessels in a subject in need thereof, comprising administering to the subject a therapeutically effective amount of a composition comprising i) an extract of *Hypericum revolutum* or ii) one or more compounds obtainable from an extract of *Hypericum revolutum* or salts or solvates thereof, wherein the composition comprises 5-dihydroxy-6-methyl-1-(3-methylbut-2-enoxy)-2-(3-methyl butyryl)-4-(2-methyl butyryl)-benzene.

4. A method of dilating blood vessels in a subject in need thereof, comprising administering to the subject a therapeutically effective amount of a composition comprising i) an extract of *Hypericum revolutum* or ii) one or more compounds obtainable from an extract of *Hypericum revolutum* or salts or solvates thereof, wherein the composition comprises 3-chloro-9a-(1-hydroxy-3-methylbut-2-en-1-yl)-8-isobutyryl-2,2,7,7-tetramethyl-6-(4-methylpent-3-enoyl) hexahydro-2H-4a,8-methanocyclohepta[b]pyran-9,10 (9aH)-dione.

5. The method of claim 1, wherein the composition is in a form selected from a tablet, capsule, or aqueous solution.

6. A tablet or capsule comprising
a composition comprising i) an extract of *Hypericum revolutum* or ii) one or more compounds obtainable from an extract of *Hypericum revolutum* or salts or solvates thereof, wherein the composition comprises 2,3,4-trimethoxy xanthone; and
a pharmaceutically acceptable carrier.

7. The method of claim 3, wherein the subject suffers from one or more of hypertension, eclampsia, preeclampsia, metabolic syndrome, angina, congestive heart failure, pulmonary arterial hypertension, and erectile dysfunction.

8. The method of claim 3, wherein the composition is in a form selected from a tablet, capsule, or aqueous solution.

9. The method of claim 4, wherein the subject suffers from one or more of hypertension, eclampsia, preeclampsia, metabolic syndrome, angina, congestive heart failure, pulmonary arterial hypertension, and erectile dysfunction.

10. The method of claim 4, wherein the composition is in a form selected from a tablet, capsule, or aqueous solution.

* * * * *